(12) United States Patent
Mukhopadhyay et al.

(10) Patent No.: US 9,133,450 B2
(45) Date of Patent: Sep. 15, 2015

(54) THERMOSTABLE ENZYMES AND METHODS OF MAKING AND USING THE SAME

(75) Inventors: Arka Mukhopadhyay, Howrah (IN); Hirak Kumar Patra, District West Midnapore (IN); Krishanu Chakraborti, Kolkata (IN); Anjan Kr. Dasgupta, Kolkata (IN); Dhrubajyoti Chattopadhyay, India (IN)

(73) Assignee: UNIVERSITY OF CALCUTTA, Kolkata (IN)

(*) Notice: Subject to any disclaimer, the term of this patent is extended or adjusted under 35 U.S.C. 154(b) by 0 days.

(21) Appl. No.: 13/991,605

(22) PCT Filed: Apr. 14, 2012

(86) PCT No.: PCT/IB2012/000744
§ 371 (c)(1),
(2), (4) Date: Jun. 4, 2013

(87) PCT Pub. No.: WO2013/114149
PCT Pub. Date: Aug. 8, 2013

(65) Prior Publication Data
US 2014/0193890 A1 Jul. 10, 2014

(30) Foreign Application Priority Data

Jan. 31, 2012 (IN) .......................... 95/2012

(51) Int. Cl.
| | |
|---|---|
| *C11C 1/00* | (2006.01) |
| *C12N 9/96* | (2006.01) |
| *C12N 9/88* | (2006.01) |
| *A23K 1/165* | (2006.01) |
| *A23L 1/015* | (2006.01) |
| *C12P 19/00* | (2006.01) |
| *C11D 3/386* | (2006.01) |
| *C11D 7/16* | (2006.01) |
| *C11D 17/06* | (2006.01) |

(52) U.S. Cl.
CPC ............... *C12N 9/96* (2013.01); *A23K 1/1653* (2013.01); *A23L 1/0153* (2013.01); *C11D 3/386* (2013.01); *C11D 7/16* (2013.01); *C11D 17/06* (2013.01); *C12N 9/88* (2013.01); *C12P 19/00* (2013.01); *C12Y 402/02002* (2013.01)

(58) Field of Classification Search
CPC ........................................................ C12N 9/88
USPC ............................................. 435/287.1, 303.2
See application file for complete search history.

(56) References Cited

U.S. PATENT DOCUMENTS

| 3,802,997 A | 4/1974 | Messing |
| 645,191 A1 | 9/2002 | Edwards |
| 6,451,591 B1 | 9/2002 | Edwards |
| 2003/0046773 A1 | 3/2003 | Xu et al. |
| 3003/0046773 | 3/2003 | Xu et al. |

FOREIGN PATENT DOCUMENTS

| CN | 101385856 | 3/2009 |
| WO | WO 00/04384 A1 | 1/2000 |
| WO | WO 03/002705 A1 | 1/2003 |

OTHER PUBLICATIONS

Spagna et al. "Immobilization of a pectinlyase from *Aspergillus niger* for application in food technology", Enzyme and Microbial Technology, 1995, 17:729-738.*
Degirmenbasi et al. "Biocomposites of nanohydroxyapatite with collagen and poly(vinyl alcohol)", Colloids and Surfaces B: Biointerfaces, 2006, 48:42-49.*
Yadav et al. "Purification and properties of an extracellular pectin lyase produced by the strain of penicillium oxalicum in solid-state fermentation", Indian J of Biochemistry and Biophysics, 2007, 44:247-251.*
Amorim, H.V., et al, "Coffee enzyme and coffee quality." In: Ori, R., St. Angelo, A.J. (Eds.), Enzymes in Food and Beverage Processing. ACS Symposium Series, (1977), vol. 47. pp. 27-56.
Basu, Snehasish, et al, "Thermodynamic characterizatin of highly termoactive extracellular pectate lyase from a new isolate Bacillus pumilus DKS1," Bioresource Technology 99 (2008) 8088-8094.
Bruhlmann, F., et al, "Pectinolytic enzymes from actinomycetes for the degumming of ramie bast fibers." Appl. Environ. Microbiol. (1994), 60(6)62107-2112.
Chesson, A., "Maceration in relation to the post handling and processing of plant material." J. Appl. Biotechnol. (1980), 48, 1-45.
Godfrey, A., "Production of industrial enzymes and some applications in fermented foods." In: Woods, B.J.B. (Ed.), Microbiology of Fermented Foods, vol. 1. Elsevier Applied Science, London, (1985), pp. 345-373.
Gomes, PJ, et al, "A highly reproducible continuous process for hydroxypatite nanoparticles synthesis." J Nanosci Nanotechnol. 2009 Jun., 9(6), 3387-95.
Holbom, B., et al, "Chemical changes in peroxide bleaching of mechanical pulps." Das Papier A 45 (10), V16-V22 (1991).
Horikoshi, K., "Enzymes of alkalophiles." In: Fogarty, W.M., Kelly, C.T. (Eds.), Microbial Enzymes and Biotechnology, second ed. Elsevier Applied Science, London, (1990), pp. 275-294.
International Search Report and Written Opinion on PCT/IB2012/000744, mailed Jul. 5, 2012.
Kashyap, D.R. et al, "Applications of pectinases in the commercial sector: a review" D Bioresource.Technology 77 (2001) 215-227.
Laemmli, et al., "Cleavage of Structural Protains during the Assembly of the Head of Bacteriophage T4," Nature 227 (1970) pp. 680-685.
Liao, C.H., et al, "Biochemical characterizaticin of pectate lyases produced by fluorescent Pseudomonads associated with spoilage of fresh fruits and vegetables." J. Appl. Microbiol., (1997),.83, 10-16.
Zhu, Lin et al., Bioconjugation of Netural Protease on Silk Fibroin Nanoparticles and Application in the Controllable Hydrolysis of Sericin, J. Agric. Food Chem. Aug. 16, 2011, 59, 10298-10302, p. 10301 section titled: "Thermal Stability".

(Continued)

*Primary Examiner* — Bin Shen
(74) *Attorney, Agent, or Firm* — Foley & Lardner LLP

(57) ABSTRACT

Provided herein are compositions and methods for enhancing enzyme activity, half-life and/or thermostability. Also provided herein are compositions and methods including the enhanced enzymes. Also provided herein are methods and compositions related to improved pectinolytic enzymes, such as pectate lyase, which exhibit enhanced activity, thermostability and/or longer half-life.

18 Claims, 9 Drawing Sheets

(56) References Cited

OTHER PUBLICATIONS

Lowrey et al., "Protein Measurement with the Folin Phenol Reagent" J. Biol. Chem (1951) 193, pp. 265-275.

Mir, Aparna et al., "Aqueous ferrofluids as templates for magnetic hydroxypatite nanocomposites," J Mater Sci: Mater Med (2010) 21, pp. 2365-2369.

Montazeri, N., et al, "Synthesis of fluoroapatite-Hydroxyapatite nanoparticles and toxicity investigation." International journal of Nanomedicine 2011: 6, 197-201.

Ortega, N., et al, "Kinetic behaviour and thermal inactivation of pectin lyase used in food processing." Int. J. Food Sci. Technol., (2004), 39, 631-639.

Reid, I., et al, "Pectinase in paper making: Solving retention problems in mechanical pulp, bleached with hydrogen peroxide." Enz. Microbiol. Technol., (2000), 26, 115-123.

Sawada, K., et al, "Enzyme processing of textiles in reverse micellar solution." Journal of Biotechnology, (2001), 89: 263-269.

Sheik, Faheem A. et al, "Synthesis of poly(vinyl alcohol) PVA nanofibers incorporating hydroxyapatite nanoparticles as future implant materials." Macromolecular research, vol. 18, No. 1, pp. 59-66 (2010).

Sieiro, Carmen et al., "Microbial Pectic Enzymes in the Food and Wine Industry," Food Industrial Processes — Methods and Equipment, Published online Feb. 2012, pp. 201-218.

Solbak, A.I., et al, "Discovery of pectin-degrading enzymes and directed evolution of a novel pectate lyase for processing cotton fabric." J. Biol. Chem., (2005), 280: 9431-9438.

Tanabe, H., et al, "Plant tissue maceration caused by pectinolytic enzymes from Erwinia spp. under alkaline conditions." Agric. Biol. Chem., (1987), 51 (10), 2845-2846.

Tanabe, H., et al, "Pretreatment of pectic wastewater from orange canning by soft-rot *Erwinia carotovora*." J. Fermentation Technol., (1986), 64, 265-268.

Tanabe, H., et al, "Pretreatment of pectic wastewater from orange canning process by an alkalophilic Bacillus sp." J. Fermentation Technol., (1987), 65 (2), 243-246.

Thornton, J., et al, "Polysaccharides dissolved from Norway spruce in thermomechanical pulping and peroxide bleaching." J. Wood Chem. Technol., (1994), 14 (2), 159-175.

Tzanov, T., et al, "Bio-preparation of cotton fabrics." Enzyme and Microbial Technology, (2001), 29: 357-362.

Roberts, D. P., et al., "Requirement for Two or More Erwinia carotovora subsp, Carotovora Pectolytic Gene Products for Maceration of Potato Tuber Tissue by *Escherichia coli*," Journal of Bacteriology, vol. 167, No. 1, pp. 279-284 (1986).

Carr, J.G., "Tea, coffee and cocoa," In: Wood, B.J.B. (Ed.), Microbiology of Fermented Foods, vol. II. Elsevier Applied Science, London, pp. 133-154 (1985).

West, S., "Olive and other edible oils," Industrial Enzymology, second ed. Stockholm Press, New York, pp. 295-300 (1996).

\* cited by examiner

THERMOSTABLE ENZYMES AND METHODS OF MAKING AND USING THE SAME

CROSS-REFERENCE TO RELATED APPLICATIONS

This application is a U.S. National Stage Application under 35 USC §371 of International Application No. PCT/IB2012/000744, filed Apr. 14, 2012, which claims priority to Indian Patent Application No. 95/KOL/2012, filed Jan. 31, 2012, the entire contents of which are hereby incorporated by reference in their entireties.

BACKGROUND

Commercial enzyme preparations used in food processing generally contain a pectate lyase enzyme component, which catalyzes chemical reactions that lead to quality improvement in food products. Because the enzyme preparations may include constituents derived from microorganisms that are used to produce this enzyme, sterility, especially in the food processing context, can be an important consideration.

Normally, high temperatures can provide sterilization. However, the high temperatures that provide sterilization can result in enzyme denaturation. Consequently, the activity of enzyme can be decreased or lost.

SUMMARY

Provided herein are compositions and methods related to enzymes having enhanced activity, half-life, and/or thermal stability.

In some aspects, an enzyme composition is provided. In some embodiments, the enzyme compositions includes at least one nanoparticle comprising an apatite moiety, and at least one enzyme in contact with the nanoparticle, the apatite moiety or both. In some embodiments, the apatite moiety includes hydroxyapatite. In some embodiments, the nanoparticle including an apatite moiety has a diameter of about 50 nm to about 200 nm.

In some embodiments, the enzyme comprises a pectinolytic enzyme. In some embodiments, the pectinolytic enzyme includes one or more of a pectate lyase, pectin lyase, polygalacturonase, polygalacturonate lyase, pectinesterase, pectinase and endopectate lyase. In some embodiments, the enzyme is a pectate lyase, pectin lyase, polygalacturonase, polygalacturonate lyase, pectinesterase, pectinase, endopectate lyase, or combinations thereof.

In some embodiments, the enzyme is derived from a microorganism, such as a bacteria or fungus. For example, in some embodiments, the enzyme is purified from one or more of *Bacillus* sp., *Aspergillus* sp., *Penicillium* sp., *Sclerotinia* sp., *Stereum* sp., *Erwinia* sp., *Amycolata* sp., *Yersinia* sp., *Fusarium* sp., *Pseudomonas* sp., *Streptomyces* sp., *Candida* sp., *Rhodotorula* sp., and *Aureobasidium* sp. In some embodiments, the enzyme is recombinantly derived. In some embodiments, the enzyme comprises a recombinant enzyme.

In some embodiments, the compositions include one or more cations. For example in some embodiments, the compositions include at least one divalent cation. In some embodiments, the divalent cation comprises calcium.

In some embodiments, the enzyme in the composition exhibits an increased activity as compared to the same enzyme that is not in contact with the nanoparticle, the apatite moiety, or both. Additionally or alternatively, in some embodiments, the enzyme in the composition is more thermostable as compared to the same enzyme that is not in contact with the nanoparticle, the apatite moiety, or both. Additionally or alternatively, in some embodiments, the enzyme in the composition has an increased activity at a higher temperature as compared to the same enzyme that is not in contact with the nanoparticle, the apatite moiety, or both. In some embodiments, the enzyme in the composition has an increased activity at a higher temperature and is more thermostable as compared to the same enzyme that is not in contact with the nanoparticle, the apatite moiety, or both. In some embodiments, the enzyme in the composition has a longer half-life as compared to the same enzyme that is not in contact with the nanoparticle, the apatite moiety, or both. In some embodiments, the enzyme includes a pectinolytic enzyme. In some embodiments, the enzyme is a pectinolytic enzyme. In some embodiments, the enzyme includes pectate lyase. In some embodiments, the enzyme is pectate lyase.

In some aspects, methods of making a thermostable enzyme composition are provided. In some embodiments, the methods include: combining to form a mixture: i) a plurality of nanoparticles, wherein at least some of the nanoparticles comprise an apatite moiety; and ii) at least one enzyme; under conditions in which the enzyme is in contact with the nanoparticles, the apatite moiety, or both. In some embodiments, the apatite comprises hydroxyapatite. In some embodiments, the enzyme includes a pectinolytic enzyme. In some embodiments, the enzyme includes a pectate lyase. In some embodiments, the method includes combining one or more divalent cations into the mixture. In some embodiments, the one or more divalent cations include one or more of $Ca^{2+}$, $Mg^{2+}$, $Mn^{2+}$, $Co^{2+}$, and $Cd^{2+}$.

In some embodiments of the method, the mixture is incubated. For example in some embodiments, the mixture is incubated at about 55° C. Additionally or alternatively, in some embodiments, the mixture is incubated for a period of about 2 to about 5 hours. In some embodiments, the incubation is carried out at a pH of about 8.5. In some embodiments, the enzyme is purified prior to combining.

In some aspects, provided herein are methods of treating a pectin-containing material. In some embodiments, the method includes contacting the material with a composition including: i) at least one nanoparticle, comprising an apatite moiety; and ii) a pectinolytic enzyme in contact with the nanoparticle, the apatite moiety, or both, for a time and under conditions wherein at least some of the pectin in the material is cleaved by the enzyme. In some embodiments, the pectin-containing material includes a textile, plant, detergent, biocomposite, wastewater, paper, oil, animal feed, food, beverage, or combinations thereof. In some embodiments, the contacting is carried out at a temperature greater than or equal to about 55° C. In some embodiments, the pectin-containing material comprises a food, and wherein the contacting is carried out at a temperature greater than or equal to 90° C. In some embodiments, the composition further comprises at least one divalent cation. In some embodiments, the nanoparticle, the apatite moiety, or both, is in contact with the pectinolytic enzyme via at least one divalent cation.

In some aspects, kits are provided. In some embodiments, the kit includes i) a pectinolytic enzyme; ii) a plurality of nanoparticles comprising an apatite moiety; and iii) instructions for combining the enzyme and the nanoparticles to form an enzyme composition. In some embodiments, the kit includes instructions for applying the enzyme composition to a pectin-containing material. Additionally or alternatively, in some embodiments, the apatite moiety comprises hydroxyapatite. In some embodiments, the pectinolytic enzyme includes pectate lyase.

The foregoing summary is illustrative only and is not intended to be in any way limiting. In addition to the illustrative aspects, embodiments, and features described above, further aspects, embodiments, and features will become apparent by reference to the following detailed description.

BRIEF DESCRIPTION OF THE DRAWINGS

FIG. 2A: without nanoparticles or $Ca^{2+}$; FIG. 2B: without nanoparticles or $Ca^{2+}$.

DETAILED DESCRIPTION

Figure 1:
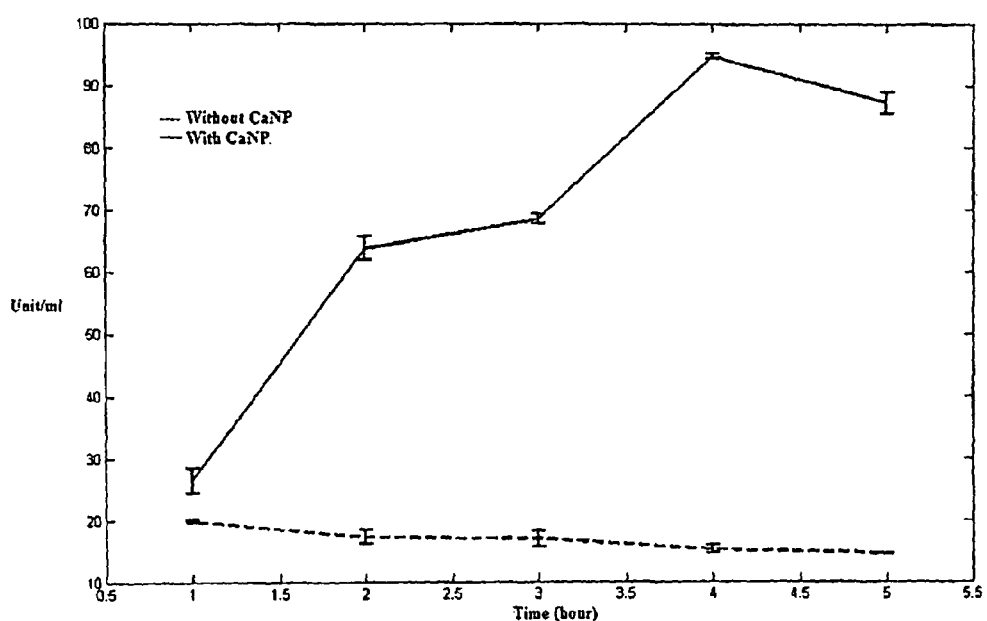
FIG. 1 shows the results of a comparative study of pectate lyase activity assay with and without hydroxyapatite nanoparticle by the Thio-Barbituric Acid (TBA) assay as a function of time after five hours of incubation.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

Disclosed herein are compositions and methods related to the manufacture and use of thermostable enzymes. In some embodiments, the enzyme compositions and methods disclosed herein include (1) one or more enzymes, such as pectinolytic enzymes; and (2) at least one nanoparticle comprising an apatite moiety. Typically, the apatite moiety, the nanoparticle or both are in contact with the enzyme.

I. Nanoparticles

The nanoparticles provided in several illustrative embodiments described herein refer to any particle in which the largest dimension is in the nanometer range, and/or in the instance wherein the composition contains a plurality of nanoparticles, the dimension described herein can refer to an average of the individual dimensions of the plurality of the nanoparticles. For example, in some embodiments, the nanoparticle has a largest dimension that is less than 1000 nm, for example, about 999 nm, about 900 nm, about 800 nm, about 700 nm, about 600 nm, about 500 nm, about 400 nm, about 300 nm, about 200 nm or about 100 nm. Additionally or alternatively, in some embodiments, the largest dimension of the nanoparticle is, for example, about 100 nm, e.g., about 90 nm, about 80 nm, about 70 nm, about 60 nm, about 50 nm, about 25 nm, about 20 nm, about 10 nm, about 5 nm, about 3 nm, about 2 nm or about 1 nm or less.

As noted above, the dimension can refer to, for example, the largest dimension of the particle. Additionally or alternatively, the dimension can refer to the smallest dimension of the particle. The particle can have any shape. For example, the nanoparticles in some embodiments can refer to particles that are at least substantially spherical. Additionally or alternatively, nanoparticles can have a shape that is an ellipsoid, cube, cylindrical, or an irregular shape. Depending on the shape, the dimension described herein can refer to any of diameter, radius, width, length, height, diagonal, and the like. Also, in the instance wherein the composition contains a plurality of nanoparticles, the dimension described herein can refer to an average of the individual dimensions of the plurality of the nanoparticles. For example, in some embodiments, the average of the individual dimensions of the plurality of nanoparticles is about 1000 nm, about 999 nm, about 900 nm, about 800 nm, about 700 nm, about 600 nm, about 500 nm, about 400 nm, about 300 nm, about 200 nm or about 100 nm. Additionally or alternatively, in some embodiments, the average of the individual dimensions of the plurality of nanoparticles is, for example, about 100 nm, e.g., about 90 nm, about 80 nm, about 70 nm, about 60 nm, about 50 nm, about 25 nm, about 20 nm, about 10 nm, about 5 nm, about 3 nm, about 2 nm or about 1 nm.

In some embodiments, the nanoparticle has a shape that is at substantially spherical and a diameter of about 2 nm to about 500 nm, e.g., about 10 nm to about 400 nm, about 25 nm to about 300 nm, about 50 nm to about 200 nm, about 80 nm to about 100 nm.

In some embodiments, the nanoparticles comprise apatite. In some embodiments, the nanoparticles comprise hydroxyapatite.

II. Apatite Moiety

As used herein, the term apatite moiety (or "apatite" for short) refers to a group of phosphate minerals, including hydroxylapatite, fluorapatite, chlorapatite and bromapatite, containing $OH^-$, $F^-$, $Cl^-$ or $Br^-$ ions, respectively, in the crystal. In some embodiments the chemical formula of the admixture of these endmembers is written as $Ca_{10}(PO_4)_6(OH,F,Cl,Br)_2$, and the crystal unit cell formulae of these individual minerals are written as $Ca_{10}(PO_4)_6(OH)_2$, $Ca_{10}(PO_4)_6(F)_2$, $Ca_{10}(PO_4)_6(Cl)_2$, and $Ca_{10}(PO_4)_6(Br)_2$.

Apatite is one of a few minerals that is produced and used by biological micro-environmental systems. Apatite is the defining mineral for 5 on the Mohs scale. Hydroxyapatite, also known as hydroxylapatite, is the major component of tooth enamel and bone mineral. In some embodiments provided herein, the apatite moiety refers to hydroxyapatite. Hydroxyapatite has the formula $Ca_5(PO_4)_3(OH)$, but is usually written $Ca_{10}(PO_4)_6(OH)_2$ to denote that the crystal unit cell comprises two entities. In some embodiments, the hydroxyapatite is in the form of a nanoparticle.

Hydroxyapatite (HPA) is considered a biomaterial, and is used, for example, as food additives and nutritional supplements. HPA nanopowder (e.g., HPA in nanoparticulate form) shows no toxic reaction and is biocompatible. Thus, HPA can be used in food products.

III. Enzyme

In some embodiments provided herein, at least one enzyme is in contact with the nanoparticle, the apatite moiety, or both. Depending on the application, the enzyme or enzyme composition can include any suitable enzyme. In some embodiments, the enzyme or enzyme composition includes a pectinolytic enzyme. As used herein, a pectinolytic enzyme (sometimes referred to as "pectin enzyme" or "pectinases") refers to an enzyme that hydrolyzes pectins.

In some embodiments, the pectinolytic enzyme comprises a pectate lyase. Pectate lyase enzyme is also synonymously known as endopectate lyase (or transeliminase), pectic acid lyase, polygalacturonate lyase, endogalacturonate transeliminase, endo-alpha-1,4-polygalacturonic acid lyase, polygalacturonic acid lyase, and alpha-1,4-D-endopolygalacturonic acid lyase.

By way of example, but not by way of limitation, pectinase can be found to be used in the fruit and textile industries. These enzymes break down complex polysaccharides of plant tissues into simpler molecules like galacturonic acids. The pectinase enzymes can be acidic or basic. Acidic pectinases, for example, can be used to decrease the cloudiness and bitterness beverages such as fruit and/or vegetable juices. Basic/alkaline pectinases can be used in the textile industry for the retting and degumming of fiber crops, production of paper, fermentation of coffee and tea, oil extractions and treatment of pectic waste water (e.g., from fruit juice industries).

In some embodiments, the pectinolytic enzyme includes one or more of a pectate lyase, pectin lyase, polygalacturonase, polygalacturonate lyase, pectinesterase, pectin lyase, pectinase, and endopectate lyase. In some embodiments, the pectinolytic enzyme is one or more of a pectate lyase, pectin lyase, polygalacturonase, polygalacturonate lyase, pectinesterase, pectin lyase, pectinase, and endopectate lyase. In some embodiments, the pectinolytic enzyme includes a pectate lyase.

The enzymes can be derived from a variety of bacterial, fungal or recombinant sources. In some embodiments, the enzymes are bacterially derived. Additionally or alternatively, in some embodiments, the enzymes are recombinantly derived, e.g., by methods known in the art. The enzyme can be obtained from various sources, including fungi and/or bacteria. For example, the enzyme can be obtained or purified from one or more of *Bacillus* sp., *Aspergillus* sp., *Penicillium* sp., *Sclerotinia* sp., *Stereum* sp., *Erwinia* sp., *Amycolata* sp., *Yersinia* sp., *Fusarium* sp., *Pseudomonas* sp., *Streptomyces* sp., *Candida* sp., *Rhodotorula* sp., and *Aureobasidium* sp.

In some embodiments, the enzyme comprises a polygalacturonase. The polygalacturonase can be obtained, or purified from, fungi and/or bacteria. For example, the polygalacturonase can be obtained from at least one of *Aspergillus japonicus, Aspergillus niger, Penicillium frequentans. Bacillus licheniformis, Sclerotinia sclerotiorum*, and *Stereum purpureum*. Additionally or alternatively, the polygalacturonase can be obtained by recombinant methods known in the art.

In some embodiments, the enzyme comprises a polygalacturonate lyase. The polygalacturonate lyase can be obtained, or purified from fungi and/or bacteria. For example, the polygalacturonase can be obtained from at least one of *Erwinia carotovora, Bacillus macerans, Amycolata* sp., *Bacillus* sp. *Yersinia enterocolitica, Bacillus* sp. TS44, *Fusarium monoliforme, Bacillus pumilus, Pseudomonas marginalis, Streptomyces thermovulgaris*, and *Candida boidinii* S2. Additionally or alternatively, the polygalacturonate lyase can be obtained by recombinant methods known in the art.

In some embodiments, the enzyme comprises a pectinesterase. The pectinesterase can be obtained, or purified from fungi and/or bacteria. For example, the polygalacturonase can be obtained from at least one of *Rhodotorula* sp., *Erwinia chrysanthemi* B341, *Aspergillus niger*, and *A. japonicus*. Additionally or alternatively, the pectinesterase can be obtained by recombinant methods known in the art.

In some embodiments, the enzyme comprises a pectin lyase. The pectin lyase can be obtained, or purified from fungi and/or bacteria. For example, the pectin lyase can be obtained from at least one of *Aspergillus niger* NCIM 548, *Aspergillus niger* A 138, *Penicillium italicum* CECT 2294, *Penicillium griseoroseum* CCT 6421, and *Aureobasidiurn pullalans* LV 10. Additionally or alternatively, the pectin lyase can be obtained by recombinant methods known in the art.

In some embodiments, the enzyme comprises a pectinase. The pectinase can be obtained, or purified from fungi and/or bacteria. For example, the pectinase can be obtained from at least one of *Bacillus* sp. DT-7, *Bacillus* sp. TS 47, *B. licheniformis, B. stearothermophilus, P. syringae* pv. *Glycinea*, and *Penicillium italicum*. Additionally or alternatively, the pectinase can be obtained by recombinant methods known in the art.

The enzyme can be an enzyme in a natural form (e.g., native enzyme) or a synthetic form, such as a recombinant enzyme. A recombinant enzyme can be, for example, a commercially available recombinant enzyme.

IV. Cations

In some embodiments, the compositions described herein include at least one cation. As used herein, a cation refers to an ion carrying at least one positive charge—e.g., one charge (i.e., univalent), two charges (i.e., divalent), three (i.e., trivalent), etc. In some embodiments, the compositions described herein have at least one divalent cation. In some embodiments, the cation is a metal ion, such as alkali metal ions, alkali earth ions, transition metal ions, and the like. In some embodiments, the cation is a univalent cation, including $Li^+$, $Na^+$, $K^+$, etc. Additionally or alternatively, the cation is a divalent cation, including $Be^{2+}$, $Mg^{2+}$, $Ca^{2+}$, $Sr^{2+}$, $Ba^{2+}$, $Ra^{2+}$, $Mn^{2+}$, $Co^{2+}$, and $Cd^{2+}$, etc. For example, in some embodiments, the divalent cation is selected from the group consisting of $Ca^{2+}$, $Mg^{2+}$, $Mn^{2+}$, $Co^{2+}$, and $Cd^{2+}$.

In some embodiments, the cation is added to a composition, for example, a composition comprising an enzyme such as a pectinolytic enzyme, and a nanoparticle comprising at least one apatite moiety. Additionally or alternatively, in some embodiments, the cation is present as a part of at least one molecule in the composition. For example, the cation can be a calcium cation of an apatite moiety. Additionally or alternatively, the cation can be a calcium cation additionally added to the apatite moiety.

V. Treatment of Enzymes with Nanoparticles Comprising an Apatite Moiety

Provided herein are methods of treating enzymes, such as pectinolytic enzymes, with nanoparticles. In some embodiments, the treatment method includes combining to form a mixture: i) a plurality of nanoparticles, wherein at least some of the nanoparticles comprise an apatite moiety; and ii) at least one enzyme; under conditions in which the enzyme is in contact with the nanoparticles, the apatite moiety, or both.

The enzyme, nanoparticles, and the apatite moiety can be as described above. In some embodiments, the treatment can further including adding (external) divalent ions (in addition to what might have otherwise been present in the apatite moiety) to the mixture. The mixture can be incubated by any suitable incubation techniques and the conditions can vary depending on the materials being incubated. For example, in one embodiment, the mixture is incubated at at least about 55° C.—e.g., about 60° C., about 65° C., about 70° C., about 75° C., about 80° C., about 85° C., or about 90° C. In another embodiment, the incubation can be carried out for a period of about 10 minutes to about 10 hours—e.g., about 10 minutes, 20 minutes, 30 minutes, 40 minutes, 50 minutes, 1 hour, 2 hours, 3 hours, 4 hours, 5 hours, 6 hours, 7 hours, 8 hours, 9 hours, 10 hours, or from about 2 hours to about 5 hours, about 3 to about 4 hours. In some embodiments, the incubation can be carried out in a slightly basic condition. For example, the incubation can be carried at a pH of at least about 6—e.g., about 6.5, about 7, about 7.5, about 8, about 8.5, about 9, about 9.5, or about 10. In some embodiments, the enzyme comprises a pectinolytic enzyme. In some embodiments, the enzyme comprises pectate lyase. In some embodiments, the nanoparticles comprise hydroxyapatite.

Depending on the enzyme being used, the treatment can further include purifying the enzyme (e.g., from a bacterial or fungal source) before it is combined into the mixture. Alternatively, purified enzyme can be readily combined with the other materials to form the mixture.

In some embodiments, treatment of enzymes with nanoparticles comprising an apatite moiety can alter the properties of an enzyme. As used herein a "treated" enzyme refers to an enzyme in contact with, or that has been contacted with, a nanoparticle comprising an apatite moiety. In some embodiments, the enzyme is in contact with at least a portion of at least one nanoparticle. Additionally or alternatively, in some embodiments, the enzyme is in contact with the nanoparticle, the apatite moiety, or both. The contact can be by various mechanisms, such as by hydrogen bonding, van der waals force, etc. In some embodiments, the nanoparticles comprise hydroxyapatite.

The treatment with nanoparticles comprising an apatite moiety (e.g., hydroxyapatite) in some embodiments can result in altered or improved thermal, stability and/or activity properties. Depending on the context and the specific properties, the improvement described herein can refer to either an increase in magnitude or decrease in magnitude of the property.

For example, in some embodiments, an enzyme treated with nanoparticles comprising an apatite moiety can have an increased activity as compared to the same enzyme that is not in contact with the nanoparticle, the apatite moiety, or both. In some embodiments, the increase can be at least about 10%, at least about 15%, at least about 20%, at least about 25%, at least about 30%, at least about 35%, at least about 40%, at least about 45%, at least about 50%, at least about 55% at least about 60%, at least about 70%, at least about 80%, at least about 90%, at least about 100%, at least about 200%, at least about 400%, at least about 600%, at least about 800%, or at least about 1000% greater than an enzyme not in contact with the nanoparticle, the apatite moiety or both. In some embodiments, the increase can be at least an order of magnitude higher, such as 10 times, 20 times, 30 times, 40 times, 50 times or more higher than an enzyme not in contact with the nanoparticle, the apatite moiety or both. The activity can be measured by any readily available techniques. For example, in some embodiments, enzyme activity is measured using absorbance after exciting the sample at 550 nm. In other embodiments, the activity can be characterized by kinetic parameters, including km, Vmax, and the activation energy, as described below. By way of example but not by way of limitation, in one embodiment, the enzyme comprises pectate lyase, and the enzyme—substrate complex (e.g., pectate lyase+PGA) and TBA results in a color compound, which is excited at 550 nm.

Additionally or alternatively in some embodiments, the treated enzyme exhibits more thermal stability as compared to the same enzyme that is not treated with the nanoparticle comprising an apatite moiety. For example, in some embodiments, treatment with nanoparticles comprising an apatite moiety can increase the thermal stability. Thermal stability can be measured and described via several metrics. For example, an increase in thermal stability can refer to an enzyme retaining its activity after being exposed to an elevated temperature for a period of time. For example in some embodiments, the treated enzyme provided in some embodiments herein retains activity after being exposed to an elevated temperature for at least 2 hours—e.g., at least 3 hours, at least 4 hours, at least 5 hours, at least 6 hours, at least 8 hours, at least 10 hours. In some embodiments, the elevated temperature refers to a temperature higher than a room temperature—e.g., at least 30° C., at least 37° C., at least 40° C., at least 45° C., at least 50° C., at least 55° C., at least 60° C., at least 65° C., at least 70° C., at least 75° C., at least 80° C., at least 85° C., at least 90° C., at least 95° C., at least 100° C., at least 105° C., at least 110° C., at least 115° C., at least 120° C. or higher. In some embodiments, the enzyme comprises a pectinolytic enzyme. In some embodiments, the enzyme comprises pectate lyase.

Additionally or alternatively, in some embodiments, an enzyme treated with nanoparticles comprising an apatite moiety can have an increased activity at a higher (or elevated) temperature as compared to the same enzyme that is not treated with the nanoparticle comprising an apatite moiety. For example, in some embodiments the increase can be at least about 10%, at least about 15%, at least about 20%, at least about 25%, at least about 30%, at least about 35%, at least about 40%, at least about 45%, at least about 50%, at least about 55% at least about 60%, at least about 70%, at least about 80%, at least about 90%, at least about 100%, at least about 200%, at least about 400%, at least about 600%, at least about 800%, or at least about 1000% greater than an enzyme not in contact with the nanoparticle, the apatite moiety or both. In some embodiments, the increase can be at least an order of magnitude higher, such as 10 times, 20 times, 30 times, 40 times, 50 times or more higher than an enzyme not in contact with the nanoparticle, the apatite moiety or both. The activity can be measured by any readily available techniques. For example, in some embodiments, enzyme activity is measured using absorbance after exciting the sample at 550 nm. In some embodiments, the elevated temperature refers to a temperature higher than a room temperature—e.g., at least 30° C., at least 37° C., at least 40° C., at least 45° C., at least 50° C., at least 55° C., at least 60° C., at least 65° C., at least 70° C., at least 75° C., at least 80° C., at least 85° C., at least 90° C., at least 95° C., at least 100° C., at least 105° C., at least 110° C., at least 115° C., at least 120° C. or higher. In some embodiments, the enzyme comprises a pectinolytic enzyme. In some embodiments, the enzyme comprises pectate lyase. In some embodiments, the nanoparticles comprise hydroxyapatite.

In some embodiments, an enzyme treated with nanoparticles comprising an apatite moiety can have a longer half-life ($t_{1/2}$) as compared to the same enzyme that is not treated with the nanoparticles. In some embodiments, the increase in half-life is at least about 10%, at least about 15%, at least about 20%, at least about 25%, at least about 30%, at least about 35%, at least about 40%, at least about 45%, at least about 50%, at least about 55% at least about 60%, at least about 70%, at least about 80%, at least about 90%, at least about 100%, at least 200%, at least 400%, at least 600%, at least 800%, at least 1000% longer as compared to the same enzyme that is not treated with the nanoparticles comprising an apatite moiety. In some embodiments, the increase can be at least an order of magnitude higher, such as 10 times, 20 times, 30 times, 40 times, 50 times, longer. In some embodiments, the enzyme comprises a pectinolytic enzyme. In some embodiments, the enzyme comprises pectate lyase. In some embodiments, the nanoparticles comprise hydroxyapatite.

V. Treatment of a Substrate Material with an Enzyme Compositions

The enzyme compositions described above can be applied to treat a pectin-containing material (e.g., a substrate). For example, in some embodiments, the method comprises: contacting the pectin-containing material with a composition comprising: i) at least one nanoparticle, comprising an apatite moiety; and ii) a pectinolytic enzyme in contact with the nanoparticle, the apatite moiety, or both, for a time and under conditions wherein at least some of the pectin in the material is cleaved by the enzyme.

The enzyme, nanoparticles, and the apatite moiety can be as described above. In some embodiments, the pectin-containing material comprises a textile, plant, detergent, biocomposite, wastewater, paper, oil, animal feed, food, beverage, or combinations thereof.

In some embodiments, the conditions in which the material is contacted with the enzyme composition are comparable to the incubation conditions described above. For example, in some embodiments, the contacting is carried out at a temperature greater than or equal to about 55° C. In some embodiments, wherein the pectin-containing material comprises a food or beverage, and the contacting can be carried out at higher temperatures, e.g., to sterilize the food. For example, in some embodiments, the contacting is at a temperature higher than 60° C., 65° C., 70° C., 75° C., 80° C., 85° C. or greater than or equal to 90° C. or 95° C.

In some embodiments, the compositions provided herein can provide robust catalyst alternatives for the breakdown of pectinaceous materials under industrial processing temperature; extraction and clarification of fruit juices and wine; treatment of industrial wastewater containing pectinaceous materials; retting or bioscouring of natural bast fibers (e.g., hemp and flax), cotton fabric, and combinations thereof.

In some embodiments, as the enhancement in enzyme activity and/or thermal stability provided by the compositions described herein can be of several orders of magnitude, high temperatures that can be employed ensures a high degree of food safety. Thus, the compositions and methods disclosed herein can be used in a number of food industry applications (e.g. fruit pulp processing, fruit juice clarification).

Furthermore, the compositions and methods disclosed herein can find usage in de-gumming of natural fiber, and in the production of pectic fragments for therapeutic use. The use of the nano-enabled process of elevating enzyme thermo stability while maintaining high activity at high temperature is not restricted to this domain alone and can be used in a number of other related industrial enzymology and agriculture related disciplines. For example, the compositions and methods provided herein can be used in the treatment of pectic wastewater, production of Japanese paper, paper making, oil extraction, coffee and tea fermentation, or a combination thereof.

VI. Illustrative Uses

A. Use of Enzyme Compositions for Scouring

On an industrial scale chemical scouring is common, which improves water absorbency and whiteness of textiles by removing non-cellulosic substances from many natural fibers. Violent, hazardous chemicals like soda-ash, oxalic acid, caustic soda, used in chemical scouring process, causes several environmental pollution as well as weaken the fiber strength.

Despite the interest in enzymatic methods for use in bioscouring processes, many enzymes currently in use suffers from a lack of scouring efficiency. Lack of scouring efficiency can arise from thermal instability and low activity of the enzyme. Thermal instability results in reduction of activity over time due to thermally induced changes in enzyme conformations. Higher temperature accelerates reduction in activity. Low activity limits the rate at which scouring can occur. Scouring efficiency can be increased by using compositions including pectinolytic enzymes having increased thermostability and enzymatic activity as described herein.

B. Retting and Degumming of Fiber Crops

Pectinolytic enzymes are often used in the retting and degumming of jute, flax, hemp, ramie, kenaff. (*Hibiscus sativa*), and coir from coconut husks. Retting is a fermentation process in which certain bacteria (e.g., *Clostridium, Bacillus*) and certain fungi (e.g., *Aspergillus, Penicillium*) decompose the pectin of the bark and release fiber. Commercially, retting is done by one of the two basic forms, and thermostable enzyme compositions as disclosed herein would be useful in such processes.

For example, ramie fibers are an excellent natural textile, but decorticated ramie fibers contain 20±35% ramie gum, which mainly consists of pectin and hemicellulose; hence it is necessary to degum fibers for meeting the requirement for textiles. The thermostable enzyme compositions disclosed herein would be useful for retting such fibers.

C. Treatment of Pectic Wastewater

The wastewater from the citrus-processing industry contains pectinaceous materials that are barely decomposed by microbes during the activated-sludge treatment. New wastewater treatment process have been developed which utilize alkalophillic microorganism. Treatment with such bacterial strains has proven to be useful in removing pectic substances from the wastewater. Additionally or alternatively, wastewater can be treated using the thermostable enzyme compositions disclosed herein to remove pectic substances. Using the disclosed enzyme compositions would have the advantages of eliminating the risk of contamination and additional effort (e.g., processes to remove the microorganisms) often associated with the use of bacterial systems.

D. Production of Japanese Paper

Alkaline pectinase produced by *Bacillus* sp, and *Erwinia carotovora*, due to its strong macerating activity, has been used for retting of Mitsumata bast. These netted basts have been used for the preparation of Japanese paper. The strength of the pulp from bacterial retting is as high as that obtained by the conventional soda-ash cooking method. The paper sheets prepared from this pulp are very uniform and soft to touch. Accordingly, the thermostable pectinolytic enzyme compositions disclosed herein would be useful in methods of preparing and manufacturing Japanese paper.

E. Paper Making

Pulp and paper mills are starting to use enzymes to solve challenges in their manufacturing processes. Papermaking is essentially a continuous filtration process in which a dilute suspension of fibers, fiber fragments (fines), and inorganic filler particles, such as clay. In the whole process polysaccharides are very troublesome material. Prominent among these polysaccharides are pectins, or polygalacturonic acids. The ability of polygalacturonic acids to complex cationic polymers (cationic demand) depends strongly on their degree of polymerization, monomers, dimers, and trimers of galacturonic acid do not cause measurable cationic demand, but hexamers and long chains have high cationic. Pectinase can depolymerize polymers of galacturonic acids, and subsequently lower the cationic demand of pectin solutions and the filtrate from peroxide bleaching. Accordingly, the thermostable pectinolytic enzyme compositions disclosed herein would be useful in methods of preparing and manufacturing pulp and paper.

For example, the enzyme composition can be combined with the liquid pulp mixture. Depending on the pulp process used (e.g., chemical pulping versus mechanical pulping), they type of pulp material used and the end product desired, the skilled artisan would add the enzyme mixture at the appropriate point in the process, and would understand, or could easily empirically determine, how much enzyme mixture to add, and how long to incubate the enzyme mixture with the pulp.

F. Oil Extraction

Oils from rape seed (Canola), coconut germ, sunflower seed, palm, kernel and olives are traditionally produced by extraction with organic solvents. The most commonly used solvent is hexane, which is a potential carcinogen. Cell-wall-degrading enzymes, including pectinase, may be used to extract vegetable oil in an aqueous process by liquefying the structural cell wall components of the oil-containing crop. Accordingly, the thermostable pectinolytic enzyme compositions disclosed herein would be useful in methods of extracting oils from various plant sources.

G. Coffee and Tea Fermentation

Pectinases play an important role in coffee and tea fermentation, Fermentation of coffee using pectinolytic microorganisms is done to remove the mucilage coat from the coffee beans. Pectic enzymes are sometimes added to remove the pulpy layer of the bean, three-fourths of which consists of pectic substances.

Fungal pectinases are also used in the manufacture of tea. Enzyme treatment accelerates tea fermentation, although the enzyme dose is typically carefully adjusted to avoid damage to the tea leaf. The addition of pectinase also improves the foam-forming property of instant tea powders by destroying tea pectins.

Accordingly, the thermostable pectinolytic enzyme compositions disclosed herein would be useful in methods of fermenting coffee and tea.

VII. Kits

The compositions and treatments methods provided herein can be used in various applications. For example, the compositions can be provided in a kit in one embodiment. The kit can comprise, for example, i) a pectinolytic enzyme; ii) a plurality of nanoparticles comprising an apatite moiety; and iii) instructions for combining the enzyme and the nanoparticles to form an enzyme composition. In some embodiments, the kit can further include instructions for applying the enzyme composition to a pectin-containing material. In some embodiments, the pectinolytic enzyme includes a pectate lyase. In some embodiments, the apatite moiety includes hydroxyapatite.

EXAMPLES

The present examples describes the purification of an exemplary pectinolytic enzyme, pectate lyase from *Bacillus*, the formation of nanoparticulate hydroxyapatite, and the manufacture of an enhanced pectate lyase enzyme composition. The examples also provide for characterization of the enhanced enzyme composition, including an evaluation of the enzyme thermostability, half-life, and activity. The skilled artisan will understand that while pectate lyase is exemplified below, other pectinolytic enzymes may be used with comparable effect.

Example 1

Purification of Pectate Lyase from *Bacillus pumilus*

Bacterial pectate lyase enzyme was purified from *Bacillus pumilus* by three consecutive processes: (1) ammonium sulphate fractionation (0-30%; 30%-80%); (2) ion exchange chromatography (CM Sepharose); and (3) gel filtration chromatography (Sephadex G-75) (Basu, et al., (2008) Technology 99: 8088-8094). Briefly, an overnight growth of the isolated pectinolytic bacterial strain was inoculated into 200 ml YP medium (NaCl 0.5%, yeast extract 1.0% and pectin 0.75%; pH 7.0) contained in 1000 ml conical flask. The flask was incubated at 30° C. on a rotary shaker (150 rpm) for 24 hours.

Pectate lyase was purified from 200 ml YP culture broth (growth conditions were as described above). Cell-free supernatant was fractionated with ammonium sulphate (0-30%; 30-80%), and the fraction containing the activity was used for further studies. The precipitate was dissolved in the minimum amount of Tris-HCl buffer (25 mM, pH 8.5) and dialysed against the same buffer. Next, 5 ml of dialysed sample was loaded onto a CM-Sepharose column (5 ml bed volume), equilibrated with Tris-HCl buffer (25 mM, pH 8.5). The column was washed with the Tris-HCl buffer containing (0-1 M) NaCl concentrations to elute the proteins. The collection was for 1 ml fractions. The protein content of each fraction was measured by the method of Lowry et al., (1951) J. Biol. Chem. 193, 265-275, and the pectate lyase activity was assayed by the method described below. The fractions showing pectate lyase activity were concentrated using a Macrosep 10 K unit and loaded onto a glass column packed with Sephadex G-75 (bed volume 30 ml) and equilibrated with the Tris-HCl buffer as above. Elution of the proteins was done using Tris-HCl buffer (25 mM, pH 8.5). The collection of the fractions and assay for protein and enzyme activity were as described above. 12% SDS-polyacrylamide gel electrophoresis (PAGE) was performed by the method of Laemmli, et al., (1970) Nature 227, 680-685. using Bio-Rad electrophoresis apparatus. Protein markers and the protein bands were stained by silver staining (Swain et: al., (1994) Electrophoresis 16, 948-951).

Example 2

Activity Assay of Pectate Lyase

The pectate lyase activities were determined by the thiobarbituric acid (TBA) assay which measured absorbance at 550 nm (Roberts et al., (1986) J. Bacterial. 167, 279-284). Suitable dilutions of the supernatant (1 ml) were added to 5 ml of PGA (polygalacturonic acid, sodium salt) solution (0.75%, w/v). The assay volumes were made up to 10.0 ml with Tris-HCl buffer (25 mM, pH 8.5) containing 1 mM $CaCl_2$ and incubated at 55° C. for 2 hours. About 0.6 ml of zinc sulphate (9.0%, w/v) and 0.6 ml sodium hydroxide (0.5 M) were then added. The samples were centrifuged (3000 g, 10 minutes) and 5.0 ml of the clear supernatant was added to a mixture of thiobarbituric acid (3.0 ml, 0.04 M) and HCl (1.5 ml, 0.1 M). The mixture was heated in a boiling water bath for 30 minutes, and the absorbance of the colored solution was measured at 550 nm against a reference cuvette which contained the same reagents as the experimental cuvette but for which the zinc sulphate and sodium hydroxide were added before adding the enzyme and substrate. One unit of activity was defined as the amount of enzyme that caused a change in the absorbance of 0.01 under the condition of the assay.

Example 3

Synthesis of Hydroxyapatite Nanoparticles

Hydroxyapatite (HPA) nanoparticles were fabricated in accordance with the methods described in Mir et al., (2010) J.

Mater. Sci. 21:2365-2369. Briefly, poly (vinyl) alcohol stabilized aqueous ferrofluids (PVA-ff) were used as nanotemplates for the crystallization of calcium hydroxyapatite (HPA). Four sets of PVA-ff-HPA nanocomposites were synthesized using 20, 40, 60 and 80 ml of PVA-ff for the same initial constituents of HPA.

a. Materials

All the chemicals used were of analytical grade. Ferric chloride ($FeCl_3.6H_2O$), ferrous chloride were purchased from Rankem, poly (vinyl) alcohol (mol wt. 44,000) (PVA) from Qualigenes, Di-ammonium hydrogen phosphate and ammonia solution (30%) from Merck and calcium nitrate $Ca(NO_3)2.4H_2O$ from Himedia.

b. Experimental Procedure

To prepare PVA-ff-HAp nanocomposites, the wet co-precipitation method was used:

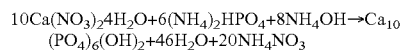

Alkaline calcium nitrate solution containing 0.5% PVA was made, to which different volumes of aqueous PVA-ff (20, 40, 60, 80 ml respectively) were added. After incubating for 24 hours, alkaline di-ammonium hydrogen phosphate was added for precipitation of HPA. The pH of the slurry was maintained at 10.5. The sample was then aged for a time period of 7 days after which the slurry was washed until pH 7 and oven dried. The powder thus obtained, was structurally and magnetically similar to that described in Mir et al., 2010.

The size and morphology of the particles were determined using transmission electron microscopy (TEM) (CM 200 CXPhilips at 160 kV). Nanoparticles (HPA crystals) had an average size of about 20 nm.

Example 4

Characterization of Untreated Pectate Lyase a. Optimum Temperature and pH of Untreated Pectate Lyase To measure the optimum temperature of pectate lyase in one testing condition, the enzyme was held at different temperatures ranging from 30° C. to 100° C. for 10 minutes. After 10 minutes, enzyme activity was determined by the TBA assay, as previously described.

To determine an optimal pH, a sample of the enzyme was placed in a buffer having pH ranging from 3-10. Enzyme activity was determined to measure optimum pH.

Figure 6A:
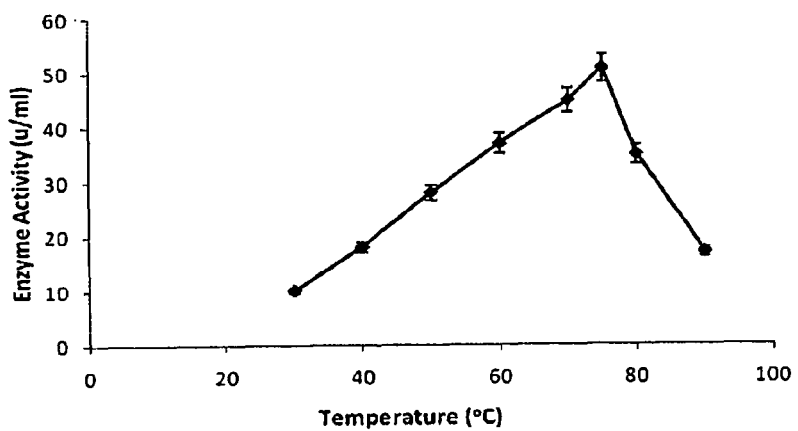
FIGS. 6(a)-6(b) illustrate the temperature and pH dependence, respectively, of pectate lyase.
Figure 6B:
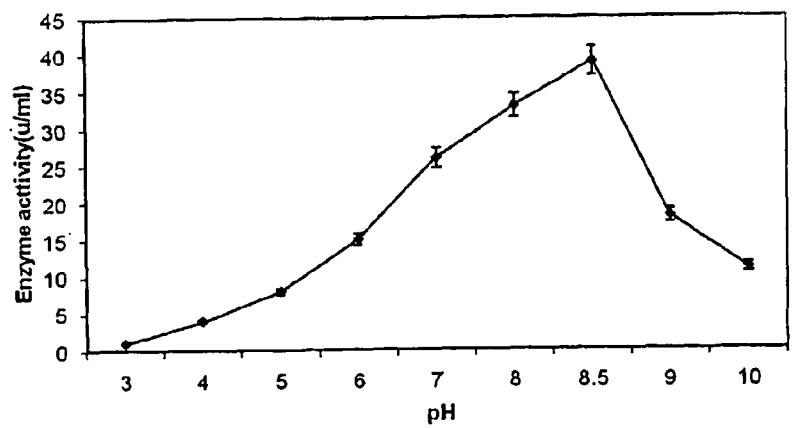

Pectate lyase was found to have a temperature optimum at 75° C. The enzyme was found to have a pH optimum at 8.5. The temperature and pH dependence of the enzyme activity are shown in FIGS. 6(A)-6(B).

b. Effect of Divalent Ions on Pectate Lyase Activity

The metal ions ($Ca^{2+}$, $Mn^{2+}$, $Mg^{2+}$, $Co^{2+}$, $Cd^{2+}$, $Ni^{2+}$ and $Zn^{2+}$) as chloride salts were added to the substrate—buffer mixture (PGA 0.75%; 25 mM Tris-HCl, pH 8.5) to give a final concentration of 1 mM, and the pectate lyase activity was measured as previously described. Each assay system contained activity of pectate lyase 93U during metal ions inhibition study.

Figure 7:
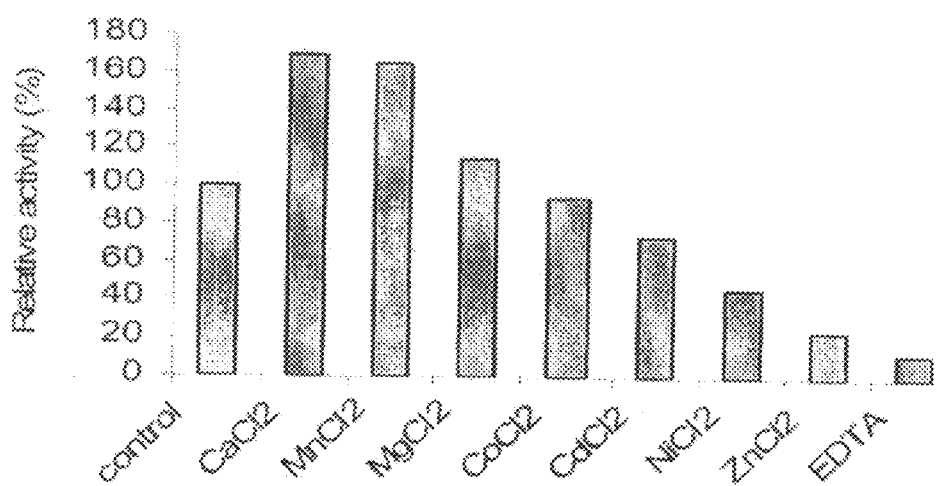
FIG. 7 is a graph showing the relative activity of pectate lyase in the presence of different cations.

The activity of pectate lyase was induced by calcium and manganese and inhibited by zinc, nickel and EDTA, FIG. 7.

Example 5

Characterization of Treated Pectate Lyase

Purified pectate lyase from *B. pumilus* (0.16 mg/ml) was incubated with poly-galactouronic acid in 25 mM TrisCl buffer (pH-8.5) for 2 hours at 55° C. Individual samples were incubated under the following four conditions (for different sets of testing specimens):

(1) in the presence of HPA nanoparticles at various concentrations;

(2) in the presence of $Ca^{2+}$ at various concentrations;

(3) in the presence of HPA nanoparticle (at 8.8 μg/ml) and $Ca^{2+}$ (at 40 μg/ml);

(4) neither HPA nanoparticle nor $Ca^{2+}$ is present.

Subsequently, the pectate lyase enzyme activity of each set was measured by using thiobarbituric acid (TBA) method described above. For the assessment of temperature and time dependence, incubation temperature and time were respectively varied.

a. HPA Nanoparticle and $Ca^{2+}$ Supplementation Enhanced the Activity of Pectate Lyase After incubating purified pectate lyase with its substrate and varying concentrations of hydroxyapatite nanoparticles in the presence or absence of $Ca^{2+}$, pectate lysase activity was measured using the TBA method described previously (absorbance at 550 nm; the enzyme—substrate complex pectate lyase+PGA and TBA yielding the color). Nanoparticle treated pectate lyase (even in absence of $Ca^{2+}$ ion in buffer) showed significantly higher activity than only $Ca^{2+}$ ion (without nanoparticle) supplemented enzyme. Moreover, only nanoparticle treated enzyme showed higher activity than both $Ca^{2+}$ supplemented (in buffer) and nanoparticle treated enzyme. The activity relations can be expressed as:

$$\text{Only HPA} > \text{HPA} + Ca^{2+} \qquad (1)$$

$$\text{Only HPA} > Ca^{2+} \qquad (2)$$

Figure 8:
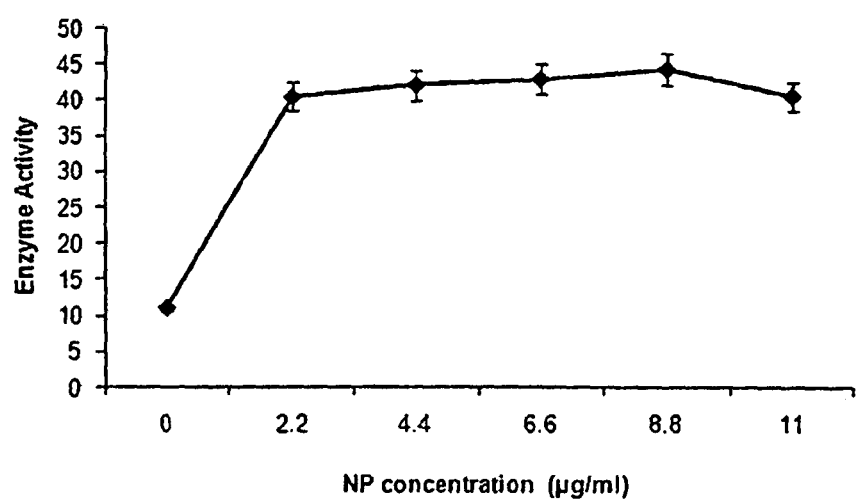
FIG. 8 is a graph showing enzyme activity with different concentrations of hydroxyapatite nanoparticles.
Figure 9:
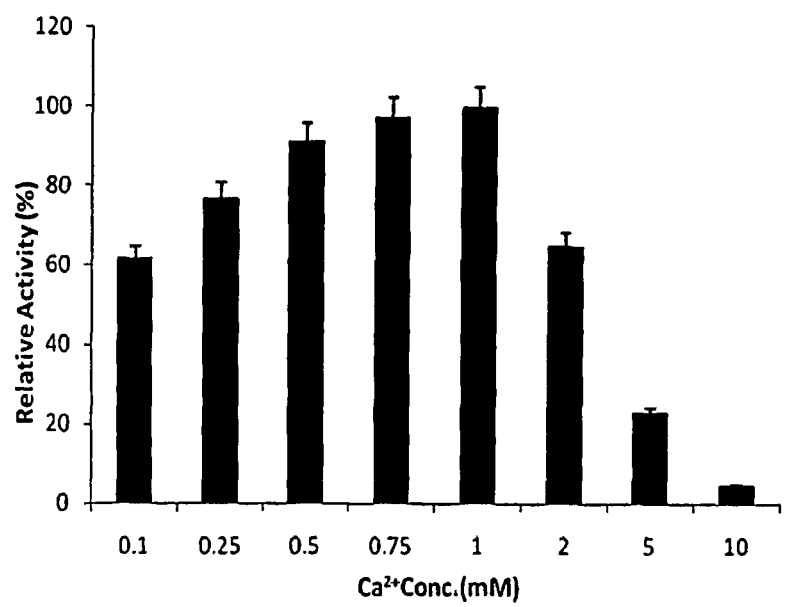
FIG. 9 shows relative enzyme activity with different concentrations of calcium.

FIG. 8 show the effect of five different concentrations of HPA nanoparticles on pectate lyase activity (2.2 μg/ml, 4.4 μg/ml, 6.6 μg/ml, 8.8 μg/ml and 11 μg/ml). It was found that within the temperature range of 50° C. to 90° C., the optimum concentration of nanoparticles was 8.8 μg/ml. FIG. 9 shows the effect of eight different concentrations of calcium on untreated pectate lyase (0.1 mM, 0.25 mM, 0.5 mM, 0.75 mM, 1 mM, 2 mM, 5 mM and 10 mM).

b. Nanoparticle Supplementation Promotes Retention of Pectate Lyase Activity

The alteration (if any) in enzyme activity with time, in the presence (8.8 μg/ml) or absence of nanoparticles, was examined via time kinetics. Pectate lyase (0.16 mg/ml) activities were measured by the TBA method for five hours at one hour intervals after incubation with substrate for two hours at 55° C.

It was observed that enzyme without nanoparticle treatment showed optimum activity at two hours, after which the activity decreased with time. However, nanoparticle treated enzyme retained activity for five hours (study end time). Furthermore, the activity was found to increase with time (FIG. 1).

It may be noted here that the experimental conditions (except for the absence and presence of NP) were identical. It is further noted that $Ca^{2+}$ is not present in either sample; fresh milliQ water was used without any extra supplementation of calcium salt in the assay system.

c. Nanoparticle Supplementation Improves Temperature Tolerance of Pectate Lyase and Augments its Activity The temperature dependence of pectate lyase activity was assessed in the presence and absence of hydroxyapatite nanoparticle. Samples were incubated for two hours at various temperatures before measuring the enzyme activity. 0.16 mg/ml of enzyme and HPA nanoparticles at 8.8 μg/ml were used.

It was found that at 90° C. the nanoparticle treated enzyme demonstrated over four times the activity of untreated enzyme.

Figures 2A, 2B:
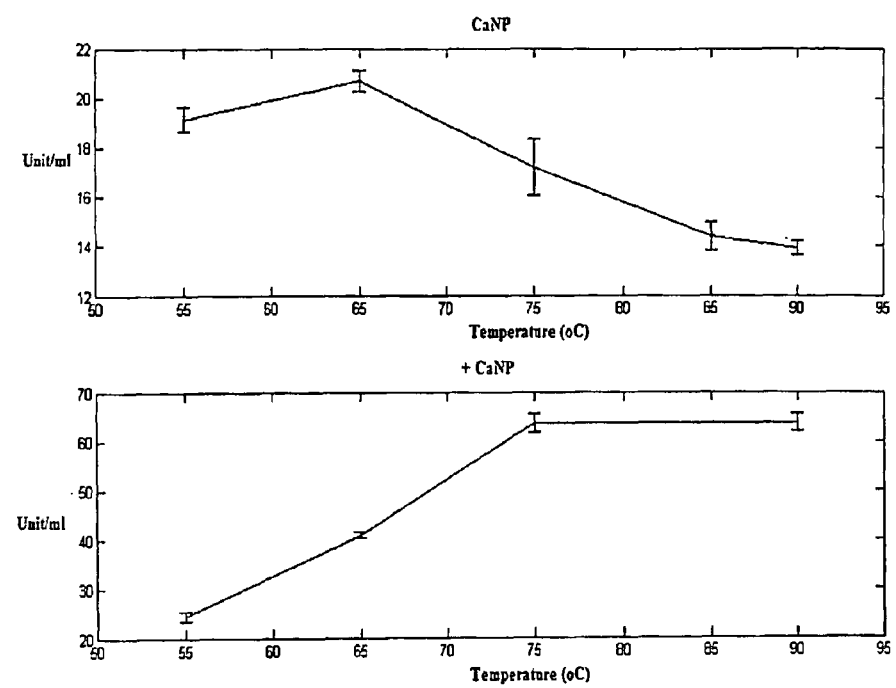
FIGS. 2A and 2B illustrate the results of a comparative study of pectate lyase activity assay with and without hydroxyapataite nanoparticles in the presence or absence of any $Ca^{2+}$ ion by TBA assay over increasing temperature (55-90° C.).

It was further found that this enhancement is not a merely transient effect. Nanoparticle treated enzyme incubated at 90° C. for 2 hours retained an activity higher than the untreated enzyme incubated at 55° C. for 2 hours (FIG. 2).

d. Substrate Specificity of Treated and Untreated Pectate Lyase

Pectate lyase can catalyze the degradation of pectin. Polygalacturonase (PG) generally hydrolyze pectic acid and pectate lyase (PL), specific for methyl esterified substrates, catalyze the cleavage of α-D-(1,4)glycosidic bonds by β-elimination of the pectin substances. Pectate lyase also acts similarly with synthetic substrate poly-galactouronic acid (PGA).

To measure the retention of enzyme activity (with PGA as substrate) at high temperature, treated pectate lyase (0.16 mg/ml enzyme and 8.8 μg/ml HPA nanoparticles) was incubated for 1-5 hours at 90° C. After the incubation, the enzyme activities were determined as above. The results were expressed relative to the values of untreated enzyme similarly incubated. The same set of experiments were performed using 0.015% apple pectin (Sigma-Aldrich) as substrate.

When pectin was used as a substrate, the activity of treated pectate lyase showed 5 fold higher activity than untreated pectate lyase after 2 hours incubation, whereas after 4 hour incubation treated pectate lyase activity was 11-fold higher than untreated pectate lyase. (Table 1). After 5 hour treated pectate lyase activity decreased 3-fold compared to the 4 hour activity. This indicates that treated pectate lyase showed enhanced activity at high temperature with both synthetic and natural substrates.

TABLE 1

Retention of activity at 90° C. by treated pectate lyase (NP-PL) and untreated pectate lyase (PL) (substrate pectin)

| Enzyme system | Pectatelyase activity after 2 hours | Pectatelyase activity after 4 hours | Pectatelyase activity after 5 hours |
|---|---|---|---|
| NP-PL | 69.54 ± 0.48 | 76.4 ± 0.65 | 26.8 ± 0.802 |
| PL | 14.8 ± 0.397 | 7.8 ± 0.54 | 4.64 ± 0.73 | e. Atomic-Absorption Spectra (AAS) Data:

The $Ca^{2+}$ concentrations of hydroxyapatite nanoparticles and 1 mM $CaCl_2$ were measured by atomic absorption spectra to compare the optimum Ca required to activate pectate lyase and stabilize it thermally.

The results are provided in Table 8. It was found that 1 mM $CaCl_2$ contain 234.3% higher $Ca^{2+}$ than hydroxyapatite nanoparticles.

TABLE 2

$Ca^{2+}$ concentration by AAS

| Parameter | Hydroxyapatite NP | 1 mM $CaCl_2$ |
|---|---|---|
| $Ca^{2+}$ concentration (μg/μl) | 0.44 ± 0.013 | 1.47 ± 0.015 |

Example 6

Kinetic Characterization of Treated and Untreated Pectate Lyase

Enzymatic reactions in industrial processes are often carried out at high temperatures in order to improve productivity and/or maintain sterility. Accordingly, the more useful or valuable enzymes are typically tolerant to (or stable at) higher temperatures. The kinetic parameters were examined to investigate the tolerance of the purified HPA treated and untreated pectate lyase to temperature. For the study of enzyme kinetics, the buffer (25 mM Tris-HCl, pH 8.5) contained no addition of external calcium ions—only HPA nanoparticle was added to each assay system. For each assay, the pectate lyase concentration was 0.16 mg/ml, and HPA nanoparticles at 8.8 μg/ml were used.

a. Determination of Km and Vmax of Treated and Untreated Pectate Lyase

The kinetic parameters, Kin, Vmax and the activation energy ($E_a$) of both HPA treated and untreated purified pectate lyase enzyme were calculated according to the methods of Liao, et al., (1997) J. Appl. Microbiol. 83, 10-16. The substrate (PGA) concentration was used from 0.015% to 1.25% to determine Km and Vmax. According to Basu et al. (2008) the optimum temperature of purified pectate lyase from DKS1 was 75° C.; thus, one set of experiments for Km and Vmax was carried out at this temperature. A separate set of experiments was also performed 90° C. Results showed high activity for treated pectate lyase (NP-pectate lyase) at 90° C.

Figure 3:
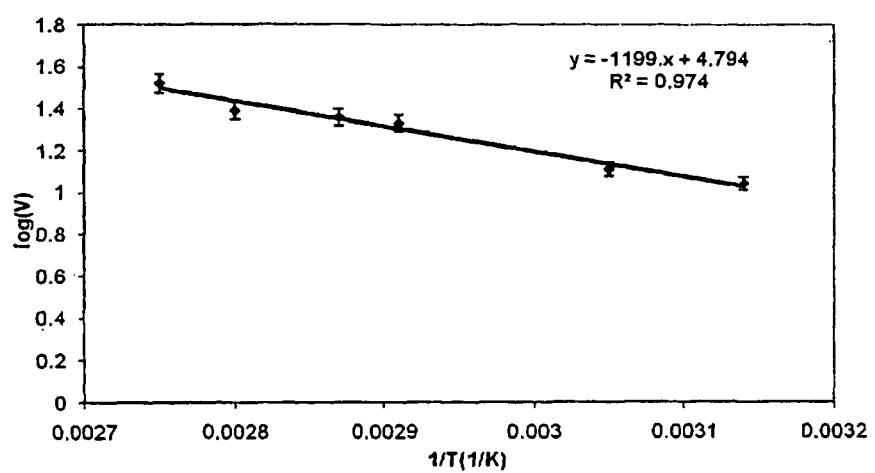
FIG. 3 shows an Arrhenius plot for heat activation for hydroxyapatite ("HPA") nanoparticle treated pectate lyase.
Figure 4:
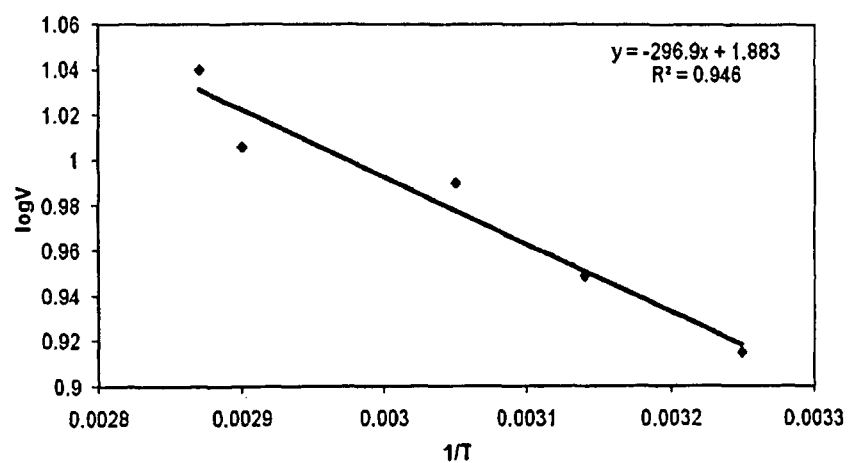
FIG. 4 shows an Arrhenius plot for heat activation for untreated pectate lyase.

The $K_m$ value decreased while the $V_{max}$ value increased in treated pectate lyase as compared to untreated pectate lyase at both 75° C. and 90° C. (Table 3). Thus, nanoparticle pretreatment enhanced enzyme-substrate affinity and lowered the activation energy compared to that of untreated enzyme. At 75° C., the $K_m$ value of treated pectate lyase decreased 63% while the Vmax increased 255.1% over the untreated pectate Lyase system. Again at 90° C. treated pectate lyase showed an 80% decreased $K_m$ value and a 716.4% increased $V_{max}$ value over the untreated pectate lyase system. Results are summarized in Table 3.

b. Determination of Activation Energy ($E_a$) of Treated and Untreated Pectate Lyase The activation energy ($E_a$) of treated and untreated pectate lyase was evaluated for the temperature range of 50-90° C. The PGA concentration used for this calculation was 0.75% (Basu et al., 2008). The activation energy ($E_a$) was calculated from the Arrhenius plots (FIGS. 3 and 4). The results are provided in Table 3.

The activation energy ($E_a$) of treated pectate lyase was found to be less than that of untreated pectate lyase. From the Arrhenius plot, untreated pectate lyase showed an $E_a$ value of −5.68 kJ/mole whereas treated pectate lyase showed a value of −22.9 kJ/mole for $E_a$. See Table 3 and FIGS. 3 and 4.

TABLE 3

Results of calculated kinetics parameters

Figure 5A:
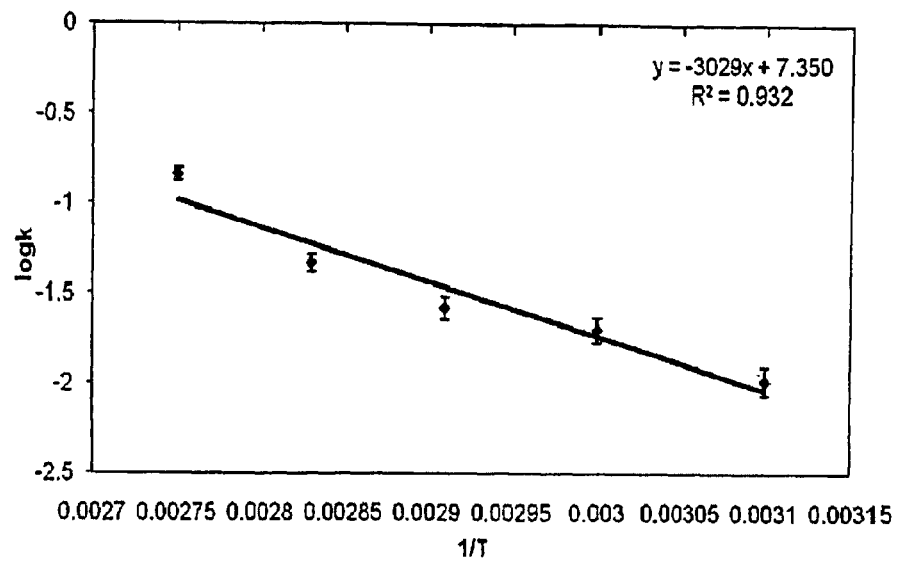
FIGS. 5(a)-5(b) show an Arrhenius plot for heat deactivation for HPA nanoparticle untreated (5A) and HPA nanoparticle treated (5B) pectate lyase.
Figure 5B:
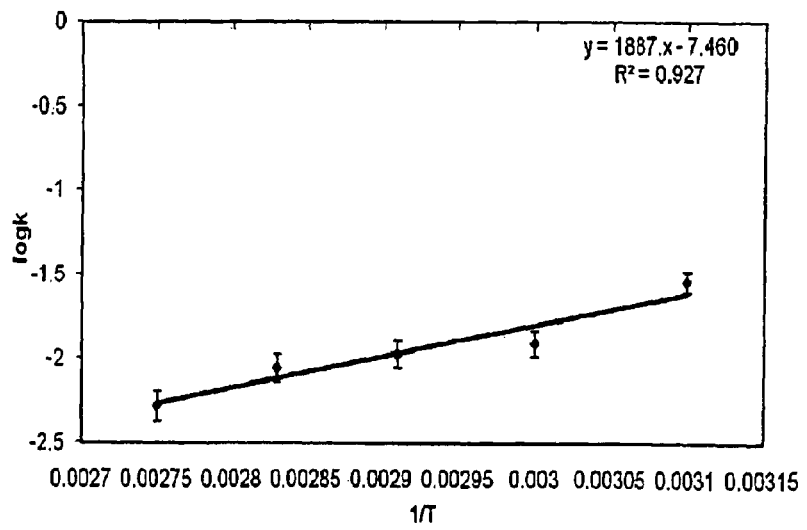

| Enzyme (PectateLyase) | Km @ 75° C. (mg/ml) | Vmax @ 75° C. (unit) | Km @ 90° C. (mg/ml) | Vmax @ 90° C. (unit) | Ea (KJmol$^{-1}$) |
|---|---|---|---|---|---|
| HPA treated | 0.05 | 610 | 0.015 | 1276 | −22.9 |
| HPA untreated | 0.3 | 214 | 0.418 | 158 | −5.68 | c. Thermotolerance and Inactivation Kinetics of Treated and Untreated Pectate Lyase The thermal inactivation of treated and untreated purified pectate lyase was examined with respect to kinetics. 0.16 mg/ml of the enzyme, pectate lyase, was treated with 8.8 μg/ml concentration of HPA nanoparticles. Untreated pectate lyase and treated pectate lyase were incubated at temperatures between 40° C. and 90° C. (313-363 K) for up to 10 minutes. Inactivation parameters comprising half-life ($t_{1/2}$), decay rate constant (k), energy of deactivation ($E_d$), enthalpy ($\Delta H$), entropy ($\Delta S$) and free energy change ($\Delta G$) were obtained according to Ortega et al. (2004) Int. J. Food Sci. Technol. 39, 631-639. The deactivation energy of both treated and untreated pectate lyase was calculated from the Arrhenius plot for heat-inactivation (heat deactivation), FIGS. 5(a)-5(b). The PGA concentration used for this purpose was 0.75%. The results of variation of kinetic parameters with the different pectate lyase systems treated and untreated with nanoparticles ("NP") are shown in Table 4-5, below and FIGS. 5(a)-5(b).

To verify the thermotolerance of pectate lyase in the presence of HPA nanoparticles, samples of the treated and untreated enzyme were pre-incubated for 10 minutes at different temperatures (30° C. to 90° C.). After the pre-incubation, the enzyme activity was determined by the TBA assay as described previously. A semi-logarithmic plot of residual activity versus time (between 50-90° C.) for treated and untreated enzyme show that the relationship is linear (data not shown). The plots indicated that untreated pectate lyase was heat inactivated with first order kinetics, but the treated enzyme was heat activated with first order kinetics. The half-life ($t_{1/2}$) values according to the plots were calculated (Tables. 4 and 5).

cations can be made therein in accordance with ordinary skill in the art without departing from the technology in its broader aspects as defined in the following claims.

The present disclosure is not to be limited in terms of the particular embodiments described in this application. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

TABLE 4

Variation of kinetic parameters for untreated pectate lyase within 50-90° C.

| Pre-Incubation Temperature (K) | Dissociation Constant [k] (min$^{-1}$) | Half Life [$t_{1/2}$] (min) | $E_d$ (kJ/mol) | $\Delta H$ (kJ/mol) | $\Delta G$ (kJ/mol) | $\Delta S$ (J/mol/k) |
|---|---|---|---|---|---|---|
| 323 | 0.01035 ± 0.00051 | 66.95 ± 2.532 |  | −60.67 ± 2.896 | 91.596 ± 0.665 | −471.4 ± 5.165 |
| 333 | 0.01988 ± 0.00186 | 34.85 ± 2.904 |  | −60.756 ± 2.72 | 92.713 ± 0.667 | −460.86 ± 3.558 |
| 343 | 0.02607 ± 0.0136 | 26.58 ± 0.581 | −57.996 ± 0.482 | −60.846 ± 3.324 | 94.804 ± 0.533 | −453.79 ± 4.935 |
| 353 | 0.047 ± 0.00451 | 14.19 ± 0.92 |  | −60.926 ± 3.324 | 102.68 ± 0.295 | −463.42 ± 3.849 |
| 363 | 0.1455 ± .00887 | 4.78 ± 0.718 |  | −61.006 ± 3.324 | 109.27 ± 0.197 | −469.07 ± 4.574 |

TABLE 5

Variation of kinetic parameters for treated pectate lyase within 50-90° C.

| Pre-Incubation Temperature (K) | Dissociation Constant [k] (min$^{-1}$) | Half Life [$t_{1/2}$] (min) | $E_d$ (kJ/mol) | $\Delta H$ (kJ/mol) | $\Delta G$ (kJ/mol) | $\Delta S$ (J/mol/k) |
|---|---|---|---|---|---|---|
| 323 | 0.0091 ± 0.0004 | 76.07 ± 1.33 |  | 33.432 ± 1.742 | 91.939 ± 0.709 | −181.13 ± 3.357 |
| 333 | 0.0123 ± 0.0004 | 56.34 ± 2.252 |  | 33.372 ± 1.742 | 94.041 ± 0.638 | −182.18 ± 4.209 |
| 343 | 0.0105 ± 0.0015 | 65.81 ± 1.563 | 36.132 ± 0.325 | 33.282 ± 1.742 | 97.389 ± 0.538 | −186.9 ± 2.425 |
| 353 | 0.0088 ± 0.0045 | 79.2 ± 0.502 |  | 33.202 ± 1.9 | 100.88 ± 0.467 | −191.72 ± 3.005 |
| 363 | 0.0052 ± 0.0005 | 133.26 ± 0.735 |  | 33.122 ± 1.545 | 105.386 ± 0.335 | −199.02 ± 2.051 |

Based on the results in Tables 4 and 5, it is shown that the addition of HPA nanoparticle increases the half-life of pectate lyase enzyme and also increases the deactivation energy ($E_d$) compared to untreated enzyme at high temperature 90° C.

HPA nanoparticle contact enhances the enzyme-substrate specificity and lowers the activation energy compared to the untreated enzyme. In addition, nanoparticle/HPA supplementation increases the half life and lowers the decay constant of pectate lyase with increasing temperature.

EQUIVALENTS

While certain embodiments have been illustrated and described, it should be understood that changes and modifi- As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 atoms refers to groups having 1, 2, or 3 atoms. Similarly, a group having 1-5 atoms refers to groups having 1, 2, 3, 4, or 5 atoms, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed:

1. A composition, comprising:
a nanoparticle, wherein the nanoparticle comprises a poly(vinyl) alcohol and an apatite moiety; and
at least one enzyme in contact with the nanoparticle, the apatite moiety, or both, wherein the enzyme comprises a pectinolytic enzyme.

2. The composition of claim 1, wherein the apatite moiety comprises hydroxyapatite.

3. The composition of claim 1, wherein the pectinolytic enzyme comprises a pectate lyase, pectin lyase, polygalacturonase, polygalacturonate lyase, pectinesterase, pectinase, endopectate lyase, or combinations thereof.

4. The composition of claim 1, wherein the pectinolytic enzyme is a pectate lyase, pectin lyase, polygalacturonase, polygalacturonate lyase, pectinesterase, pectinase, endopectate lyase, or combinations thereof.

5. The composition of claim 1, wherein the enzyme is purified from one or more organisms selected from the group consisting of *Bacillus* sp., *Aspergillus* sp., *Penicillium* sp., *Sclerotinia* sp., *Stereum* sp., *Erwinia* sp., *Amycolata* sp., *Yersinia* sp., *Fusarium* sp., *Pseudomonas* sp., *Streptomyces* sp., *Candida* sp., *Rhodotorula* sp., and *Aureobasidium* sp.

6. The composition of claim 1, wherein the pectinolytic enzyme comprises a recombinant pectinolytic enzyme.

7. The composition of claim 1, further comprising at least one monovalent cation, wherein the monovalent cation is selected from the group consisting of $Li^+$, $Na^+$, and $K^+$.

8. The composition of claim 1, wherein the pectinolytic enzyme in the composition exhibits one or more of the following characteristics:
increased activity as compared to the same pectinolytic enzyme that is not in contact with the nanoparticle, the apatite moiety, or both;
more thermostable as compared to the same pectinolytic enzyme that is not in contact with the nanoparticle, the apatite moiety, or both;
increased activity at a higher temperature as compared to the same pectinolytic enzyme that is not in contact with the nanoparticle, the apatite moiety, or both;
increased activity at a higher temperature and is more thermostable as compared to the same pectinolytic enzyme that is not in contact with the nanoparticle, the apatite moiety, or both; and
longer half-life as compared to the same pectinolytic enzyme that is not in contact with the nanoparticle, the apatite moiety, or both.

9. A composition, comprising:
a nanoparticle, wherein the nanoparticle comprises a poly(vinyl) alcohol and an apatite moiety;
at least one enzyme in contact with the nanoparticle, the apatite moiety, or both, wherein the enzyme comprises a pectinolytic enzyme; and
at least one divalent cation, wherein the divalent cation is selected from the group consisting of $Ca^{2+}$, $Mg^{2+}$, $Mn^{2+}$, $Co^{2+}$, and $Cd^{2+}$.

10. The composition of claim 9, wherein the apatite moiety comprises hydroxyapatite.

11. The composition of claim 9, wherein the pectinolytic enzyme comprises a pectate lyase, pectin lyase, polygalacturonase, polygalacturonate lyase, pectinesterase, pectinase, endopectate lyase, or combinations thereof.

12. The composition of claim 9, wherein the pectinolytic enzyme is a pectate lyase, pectin lyase, polygalacturonase, polygalacturonate lyase, pectinesterase, pectinase, endopectate lyase, or combinations thereof.

13. The composition of claim 9, wherein the enzyme is purified from one or more organisms selected from the group consisting of *Bacillus* sp., *Aspergillus* sp., *Penicillium* sp., *Sclerotinia* sp., *Stereum* sp., *Erwinia* sp., *Amycolata* sp., *Yersinia* sp., *Fusarium* sp., *Pseudomonas* sp., *Streptomyces* sp., *Candida* sp., *Rhodotorula* sp., and *Aureobasidium* sp.

14. A method of treating a pectin-containing material, the method comprising:
contacting the pectin-containing material with a composition comprising:
at least one nanoparticle, comprising a poly(vinyl) alcohol and an apatite moiety, and
a pectinolytic enzyme in contact with the nanoparticle, the apatite moiety, or both, for a time and under conditions wherein at least some of the pectin in the material is cleaved by the pectinolytic enzyme.

15. The method of claim 14, wherein contacting the pectin-containing material with the composition comprises contacting the pectin-containing material selected from a textile, plant, detergent, biocomposite, wastewater, paper, oil, animal feed, food, beverage, or combinations thereof.

16. The method of claim 15, wherein contacting the pectin-containing material with the composition comprises contacting the food, and wherein the contacting is carried out at a temperature greater than or equal to 90° C.

17. The method of claim 14, wherein the contacting is carried out at a temperature greater than or equal to about 55° C.

18. The method of claim 14, wherein contacting the pectin-containing material with the composition comprises contacting with a composition that comprises at least one divalent cation.

* * * * *